(12) United States Patent
Sundaresh

(10) Patent No.: US 8,217,216 B2
(45) Date of Patent: Jul. 10, 2012

(54) FIRST AID STRIPS CALLED: FIRST AID HATS / FIRST AID CAPS

(76) Inventor: Hoskote B. Sundaresh, Germantown, MD (US)

(*) Notice: Subject to any disclaimer, the term of this patent is extended or adjusted under 35 U.S.C. 154(b) by 1509 days.

(21) Appl. No.: 09/924,075

(22) Filed: Aug. 8, 2001

(65) Prior Publication Data

US 2003/0093023 A1    May 15, 2003

(51) Int. Cl.
*A61F 13/00* (2006.01)
(52) U.S. Cl. ............... 602/42; 602/41; 602/48; 602/52; 602/54; 602/58
(58) Field of Classification Search ............... 602/41–59, 602/888, 889; D24/189; 128/888, 889, 893, 128/894

See application file for complete search history.

(56) References Cited

U.S. PATENT DOCUMENTS

| | | | | | |
|---|---|---|---|---|---|
| 4,641,643 | A | * | 2/1987 | Greer | 602/54 |
| 4,909,243 | A | * | 3/1990 | Frank et al. | 604/304 |
| 5,086,763 | A | * | 2/1992 | Hathman | 602/42 |
| 5,533,962 | A | * | 7/1996 | Peterman et al. | 602/54 |
| 5,702,356 | A | * | 12/1997 | Hathman | 602/41 |
| 6,066,773 | A | * | 5/2000 | Freeman | 602/52 |

FOREIGN PATENT DOCUMENTS

WO    95/17146    *  6/1995

* cited by examiner

*Primary Examiner* — Kim M Lewis
(74) *Attorney, Agent, or Firm* — Monty Simmons; Simmons Patents (57) ABSTRACT

First aid hats/First aid caps are a cost effective and economical method for treating any systemic illness or topical skin condition such as boil, bruise, or burn, using first aid strips, by providing a pouch which provides a means to use medication in the form of cream or gel. The provision of a pouch prevents medication from escaping when applied on the body with an adhesive first aid strip. Thus a measured amount of any medication when applied stays where it is applied and not lost. A ring made of rubber/latex is used to create the said pouch, when placed on the first aid strip.

5 Claims, 13 Drawing Sheets

FIRST AID STRIPS CALLED: FIRST AID HATS / FIRST AID CAPS

FIELD OF INVENTION

This invention relates to first aid strips.

BACKGROUND OF THE INVENTION

A first aid strip known in the art comprises a strip of sterile, non adherent gauze pad, to one side of which is attached a strip of adhesive tape. The adhesive tape is used to fix the gauze pad over the wound on the skin of a patient. The drawback of this known art is that if some medicine in the form of, gel, ointment, cream, is applied to the skin and the first aid strip is applied over the skin, the medicine squishes out/oozes out. As a result very little to no medicine is left behind over the skin wound. Further, if there is some localized swelling or bulge, associated with the wound or skin condition, such as due to a deep cut, or when there is a wart or a raised mole over the skin, the medicine oozes out even more.

PRIOR ART

U.S. Pat. No. 4,641,643 issued to Greer discloses a bandage comprising a flexible body having a central opening, a water repellant layer overlying said body and a removable cover attached to the water repellant layer.

U.S. Pat. No. 4,909,243 issued Frank et al. relates to a dressing comprising a base plate having a through hole, a wound pad inserted in said hole, and means for attaching, the pad in the hole.

The bandage disclosed in U.S. Pat. No. 5,086,763 issued to Hathman comprises a soft-pad frame having an opening and fixed to an adhesive tape having a registering hole, a pad frame having a registering hole and secured to the soft pad frame, said pad being made of a fabric adapted to a micro hook material, a gauze pad fitted in said openings, and a removable flap having micro hook material detachably secured to the pad frame and gauze pad.

U.S. Pat. No. 5,702,356 issued to Hathman relates to a dressing comprising an adhesive strip base member having an aperture, a stepped standoff member interposed between the base member and a sealing cover member, and fitting into a first stepped member of the standoff member and in abutment registry with a second stepped member of the standoff member, means for securing the sealing cover member to the base member, and means of closing the sealing cover member to the base member.

U.S. Pat. No. 6,066,773 issued to Freeman discloses a dressing comprising an occlusive layer having an edge portion and a hydro-colloid containing polymeric support layer overlying said edge portion

SUMMARY OF THE INVENTION

Some of the objects and advantages of the invention will now be set forth in the following description, while other objects and advantages of the invention may be obvious from the description, or may be learned through practice of the invention.

The dressings of prior art appear to be complicated to manufacture. There is a necessity for a dressing which is easy to manufacture and is cost-effective while addressing the drawbacks of prior art devices.

Accordingly, the present invention provides a first aid strip comprising a strip of sterile, non-adherent gauze pad, a pouch, well, depression or hollow provided on one side of the gauze pad, which comes into contact with the skin when applied over a wound or swelling and a strip of adhesive tape attached to the other side of gauze pad for fixing the first aid strip on the skin.

In one embodiment of this invention at least two additional layers of sterile non-adherent gauze pad strips, are fixed to the gauze pad, on said one side, over the existing gauze pad layer, which comes in contact with the skin, a hole/window being provided in each of the two additional layers, to form said pouch, well, depression, or hollow. Instead of two additional layers, a single layer of appropriate thickness of gauze pad may be used instead, to achieve the same result.

The pouch, well, depression, or hollow has a shape conforming to the shape of the gauze pad and a depth of approximately 1.5-2.00 mm.

In a second embodiment of the invention, a ring of inert material is interposed between the gauze pad and the additional layers of gauze pad and sealed, creating a pouch.

In a third embodiment, a bulge is provided in said gauze pad and adhesive tape. The said bulge projecting outwardly from said other side of the first aid strip.

In the fourth embodiment a ring made of an inert material is located on top of the gauze pad strip, the outer border of the ring being flush with the margins of the gauze pad strip, on the said other side of the first aid strip. The ring preferably has an approximate depth of: 2.00-2.50 mm.

In the fifth embodiment a ring of inert material is attached to the adhesive tape, such that its inner margins surrounds the gauze pad strip, which is fixed to the adhesive tape. The shape of the ring conforms to the shape of the gauze pad strip. The ring has an approximate depth of 2.00-2.50 mm.

The present invention also provides a method for the manufacture of a first aid strip, comprising:
a) providing at least two layers of sterile non-adherent gauze pad;
b) cutting a hole or window in each of said two layers from around the, central area in a shape that conforms to the shape of the gauze pad strip;
c) providing a strip of sterile non-adherent gauze pad with no window or hole cut out, which is attached to a strip of adhesive tape;
d) attaching the said two layers of gauze pad, with a widow created in it, over the said gauze pad strip with no window of hole created in it, on the side of the gauze pad which comes in contact with the skin, to which the adhesive tape of the first aid strip is to be fixed, the said layers of gauze pad overlying each other, and overlying gauze pad strip, on said one side of said gauze pad strip; and
e) attaching a strip of adhesive tape to the other side of the gauze pad strip;

In a variant, the method comprises the steps of:
a) providing a strip of sterile, non-adherent gauze pad;
b) placing a ring made of an inert material around said gauze pad strip on the side of the gauze pad strip which comes in contact with the skin; and
c) attaching a strip of adhesive tape on the other side of the gauze pad strip to fix the ring on the gauze pad strip.

Another variant to the above methods for manufacturing a first aid strip comprises the steps of: including a strip of sterile non-adherent gauze pad, over which a ring of rubber, latex, or cork is placed, on the side which comes in contact with the skin, with its outer border flush with the margins of the said strip of gauze pad, and a strip of adhesive tape is fixed to the side of gauze pad strip not coming in contact with the skin.

In a further alternative, two layers of gauze pad strip are placed one over the other, and a ring made of an inert material is interposed between the two layers and sealed, thereafter a strip of adhesive tape is attached to one of the layers.

The present invention further provides a gauze hat or gauze cap, comprising a flat sterile gauze pad, with a pouch, well, depression, or hollow, provided on one side thereof. The well pouch, depression, hollow maybe in the form of a window or hole, formed in at least two layers of gauze pad attached to one of the sides of said gauze pad. This window or hole can be first made in the two layers of additional gauze. Then the layers maybe placed on the flat gauze pad so that the window or holes are in alignment and form a pouch, well or depression or hollow on one side of the gauze pad. Thereafter the flat gauze pad and the two additional layers are attached to one another.

In another embodiment, a ring made of inert material is interposed and sealed between the flat gauze pad and the additional layer of gauze pad.

In an alternative, the gauze hat or gauze cap comprises a flat gauze pad, and a ring of inert material such as cork, latex, rubber, attached to one side of the flat gauze pad, to form said pouch, well, depression, or hollow. In this case the outer periphery of the ring will be flush, with the margins of the gauze pad.

In yet mother embodiment, a pouch is formed as a bulge in the flat gauze pad.

Additional objects and advantages of the present invention are set forth in the detailed description herein or will be apparent to those skilled in the art upon reviewing the detailed description. Also, it should be further appreciated that modifications and variations to the specifically illustrated, referenced, and discussed steps, or features hereof may be practiced in various uses and embodiments of this invention without departing from the spirit and scope thereof, by virtue of the present reference thereto. Such variations may include, but are not limited to, substitution of equivalent steps, referenced or discussed, and the functional, operational, or positional reversal of various features, steps, parts, or the like. Still further, it is to be understood that different embodiments, as well as different presently preferred embodiments, of this invention may include various combinations or configurations of presently disclosed features or elements, or their equivalents (including combinations of features or parts or configurations thereof not expressly shown in the figures or stated in the detailed description). Those of ordinary skill in the art will better appreciate the features and aspects of such embodiments, and others, upon review of the remainder of the specification.

BRIEF DESCRIPTION OF THE DRAWINGS

A full and enabling description of the present subject matter, including the best mode thereof, directed to one of ordinary skill in the art, is set forth in the specification, which makes reference to the appended figures, in which:

FIG. 17b Shows a top view of the embodiment depicted in FIG. 17a; and

Repeat use of reference characters throughout the present specification and appended drawings is intended to represent the same or analogous features or elements of the present technology.

DETAILED DESCRIPTION OF THE INVENTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment. Thus, it is intended that the present invention covers such modifications and variations as come within the scope of the appended claims and their equivalents. Other objects, features, and aspects of the present invention are disclosed in or may be determined from the following detailed description. Repeat use of reference characters is intended to represent same or analogous features, elements or steps. It is to be understood by one of ordinary skill in the art that the present discussion is a description of exemplary embodiments only, and is not intended as limiting the broader aspects of the present invention.

Figure 1:
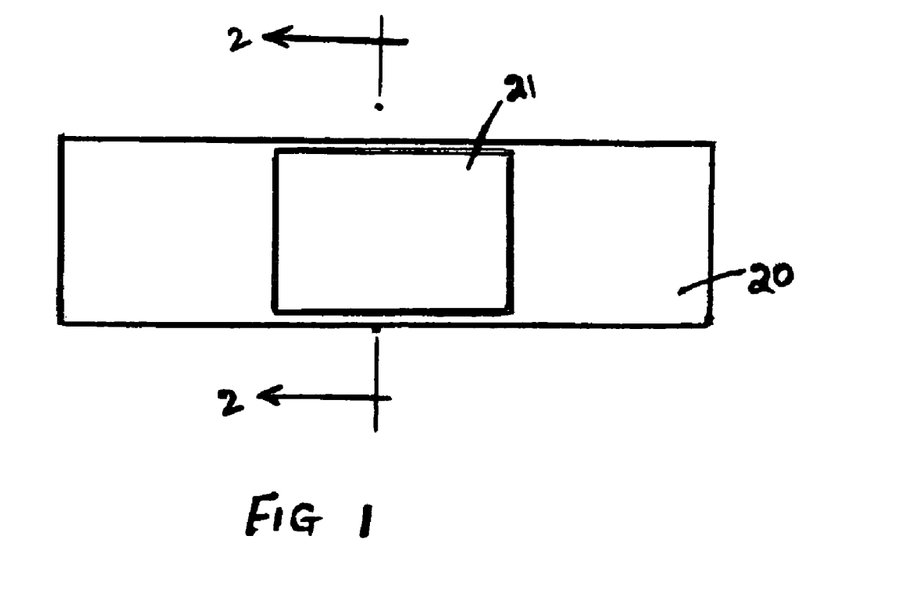
FIG. 1 Shows a first aid ship.
Figure 2:
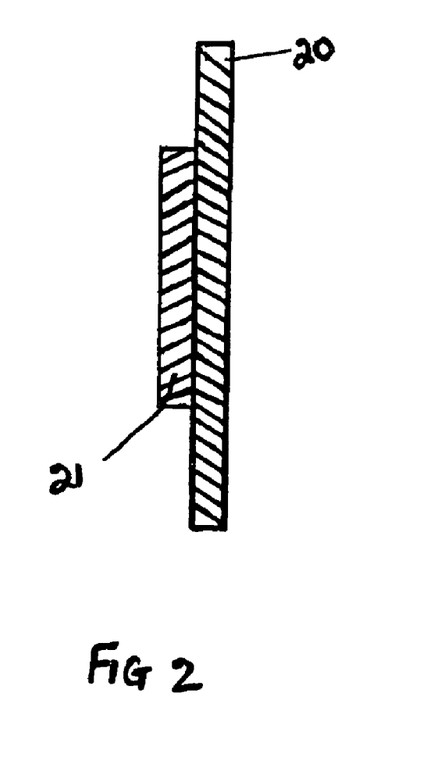
FIG. 2 Shows cross-sectional view of the first aid strip along section line, 2-2 in FIG. 1.
Figure 3:
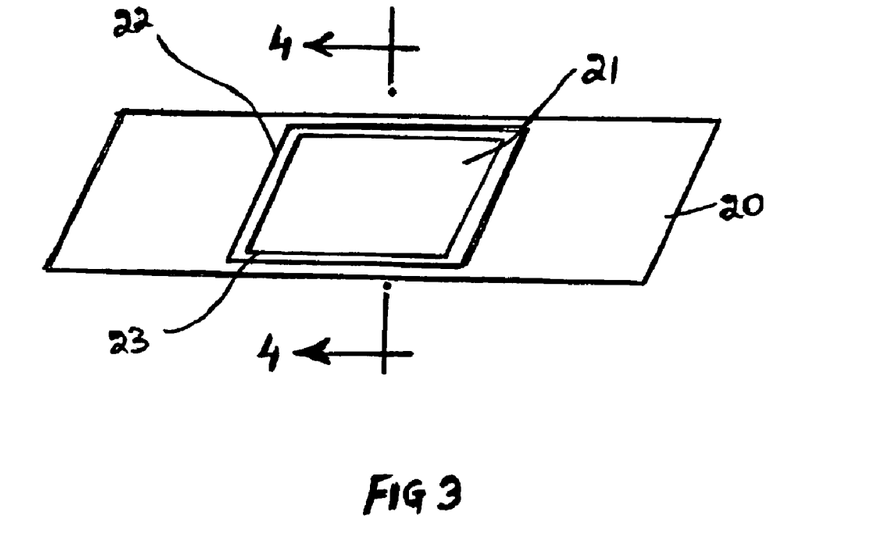
FIG. 3 Shows a tangential view, of one embodiment of the first aid strip according to present invention.
Figure 4:
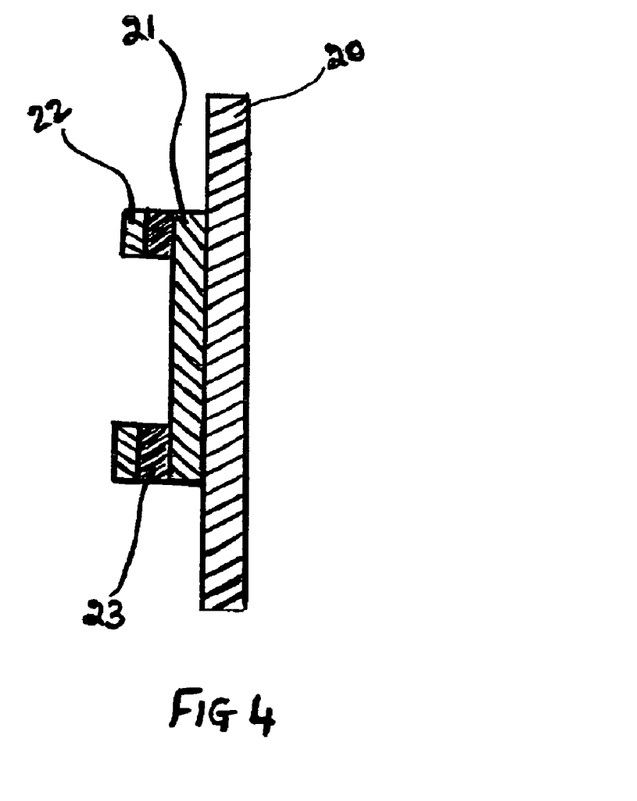
FIG. 4 Shows a cross-sectional view of the first aid strip along section line, 4-4 in FIG. 3.
Figure 5:
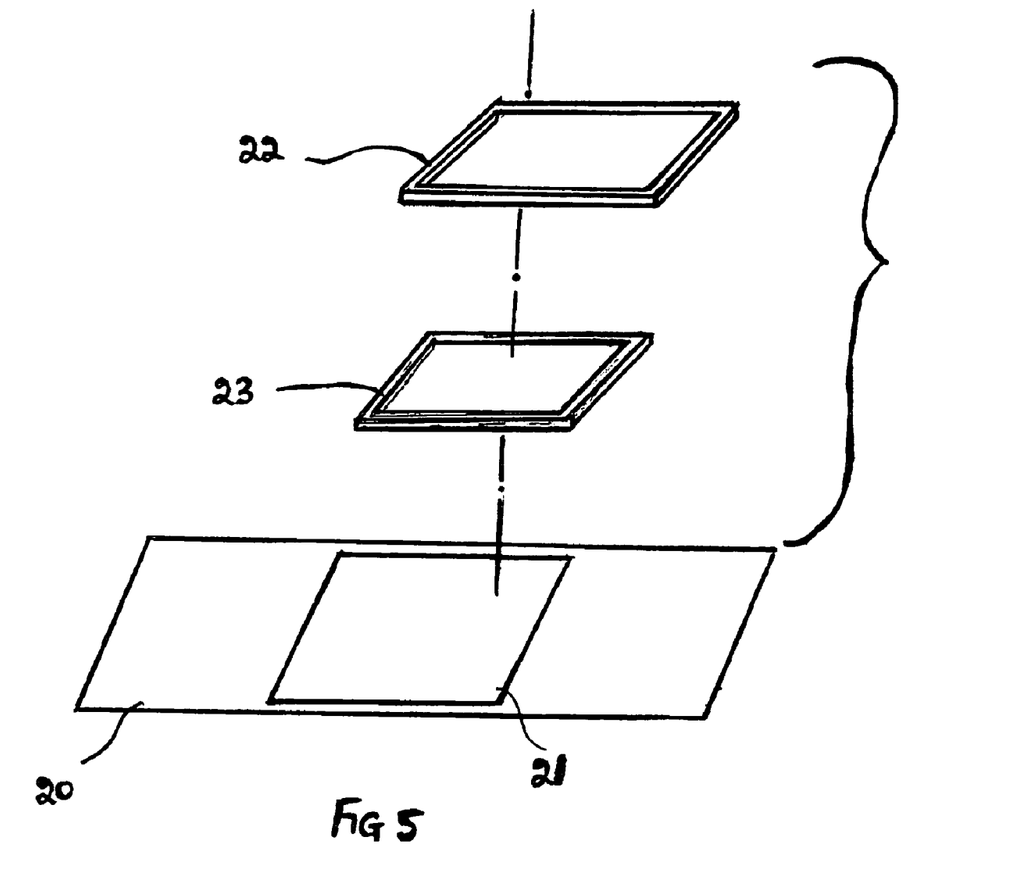
FIG. 5 Shows an exploded view of the components of the first aid strip shown in FIG. 3.
Figure 5B:
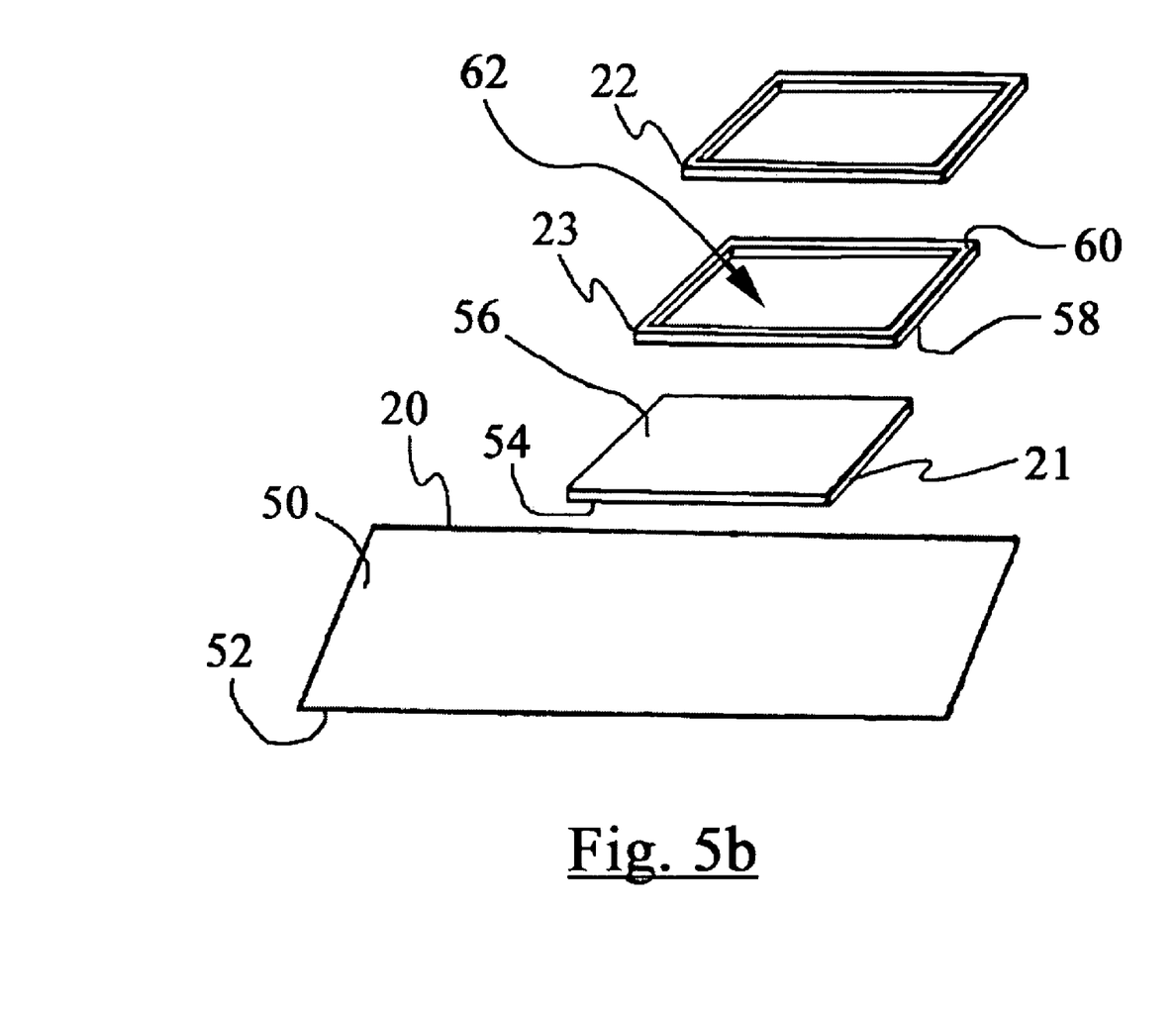
Figure 5C:
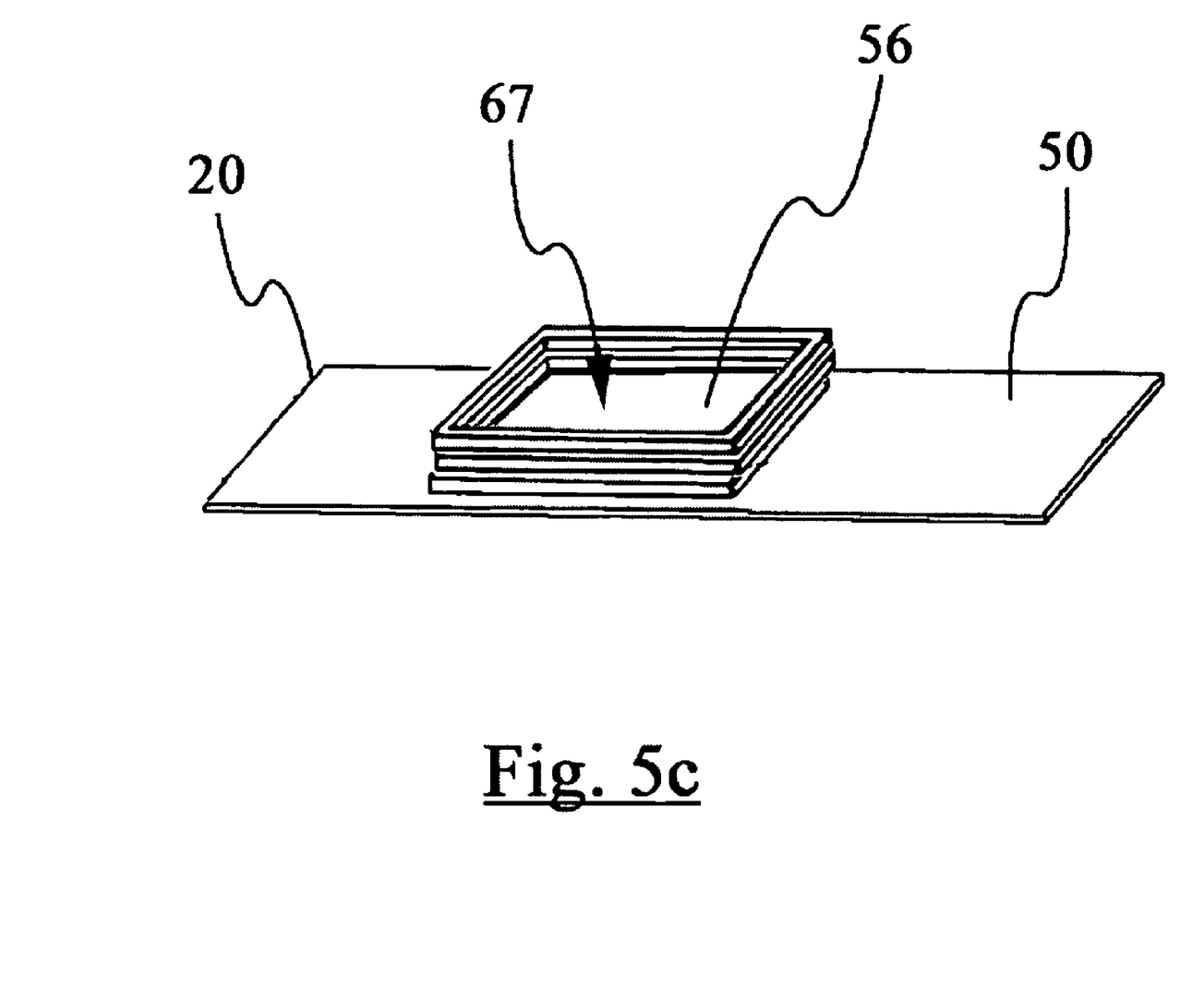

In the first embodiment shown in FIG. 1 though FIG. 5, the first aid strip comprises an adhesive tape 20, a gauze pad strip 21 attached to the adhesive tape, and two gauze pad layers 22, 23. The layers 22, 23 are each provided with a window or hole, to form a pouch, when placed over the gauze pad strip 21, and surrounded by the walls of the gauze pad layers 22, 23. They are stacked one above the other over the gauze pad strip 21, so that the windows in the different layers are aligned with one another.

The windows are cut out, from around the central area of the gauze pad layer 22, 23. The pouch thus created has an approximate depth of 1.5-2.00 mm. All the measurements are approximate and may be modified as needed.

Figure 6:
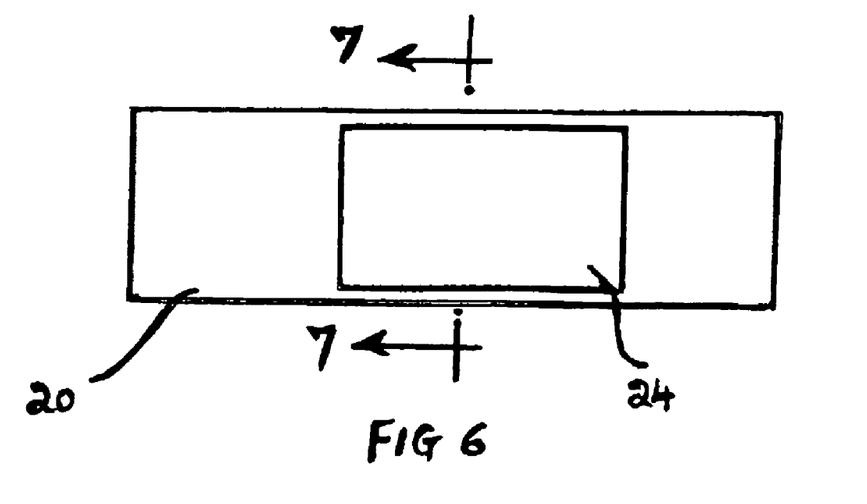
FIG. 6 Shows a plain view of a second embodiment of the present invention.
Figure 7:
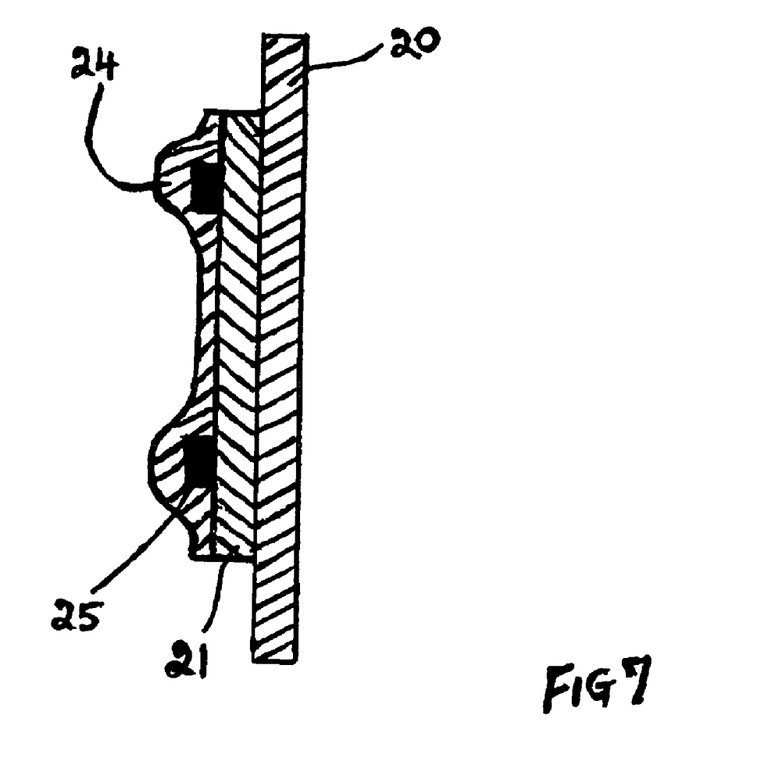
FIG. 7 Shows a cross-sectional view along section line 7-7 in FIG. 6.
Figure 8:
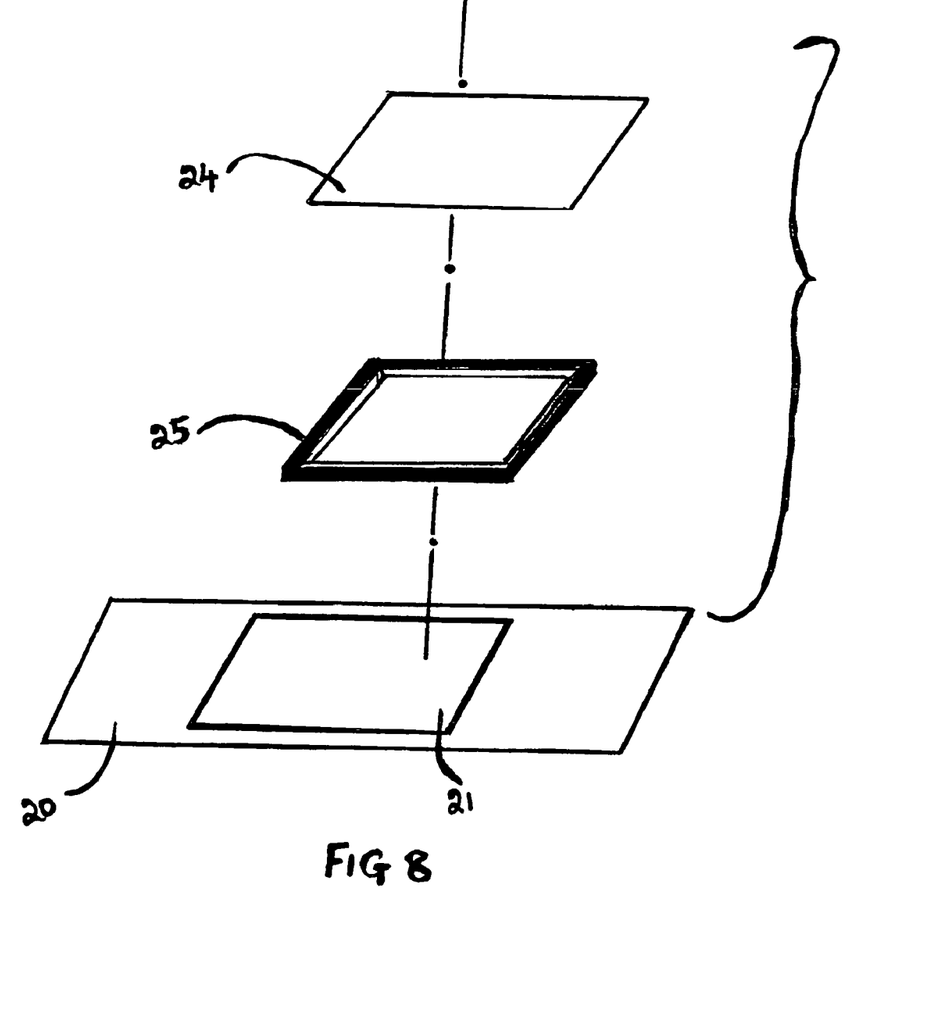
FIG. 8 Shows an exploded view of the components of the first aid strip shown in FIG. 6.

In the second embodiment shown in, FIG. 6 through FIG. 8, the first aid strip comprises an adhesive tape 20 associated with a gauze strip 21 (FIG. 7). Associated with a surface of gauze strip 21 is a ring 25. A layer of gauze pad 24 is disposed over gauze strip 21 and ring 25 thereby sealing ring 25 between gauze pad layer 21 and 24 so that it does not come in contact with the skin with the strip is associated with a wound.

For the presently preferred embodiment, ring 25 is an inert material, such as cork, rubber, or latex interposed and fixed between the gauze pad layer 21 and 24. The ring should preferably have a depth of 1.5-2.00 mm. The dimensions of the ring 25 are less than the dimensions of the gauze pad.

Figure 9:
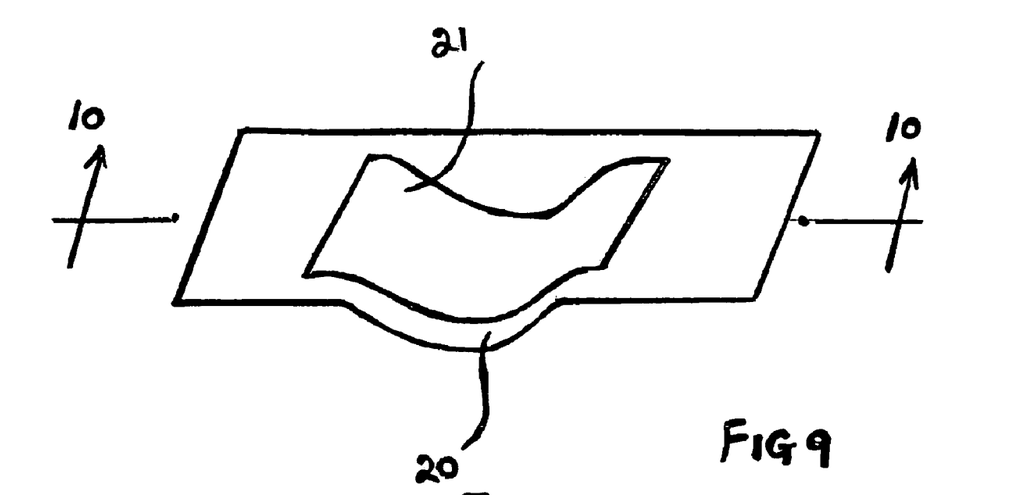
FIG. 9 Shows a tangential view of a third embodiment of the first aid strip according to the present invention.
Figure 10:
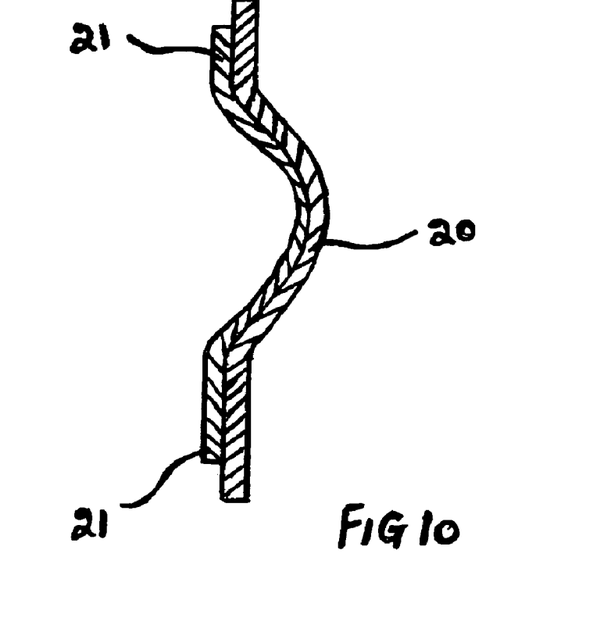
FIG. 10 Shows a cross sectional view along section line 10-10 in FIG. 9.

In the third embodiment shown in FIG. 9 though FIG. 10, the first aid strip has an adhesive tape 20 associated with a gauze pad strip 21. The tape 20 and gauze pad 21 are both extruded outwards to create a bulge.

Figure 11:
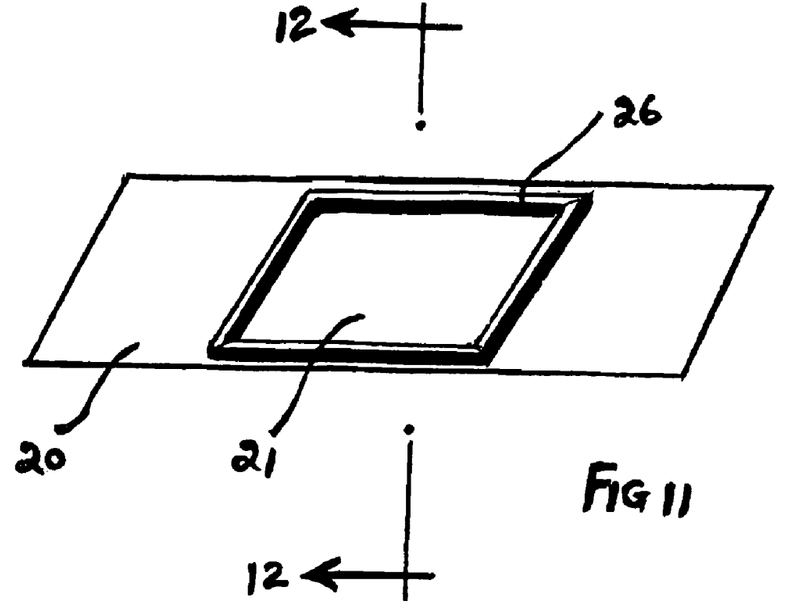
FIG. 11 Shows tangential view of a fourth embodiment of the first aid strip.
Figure 12:
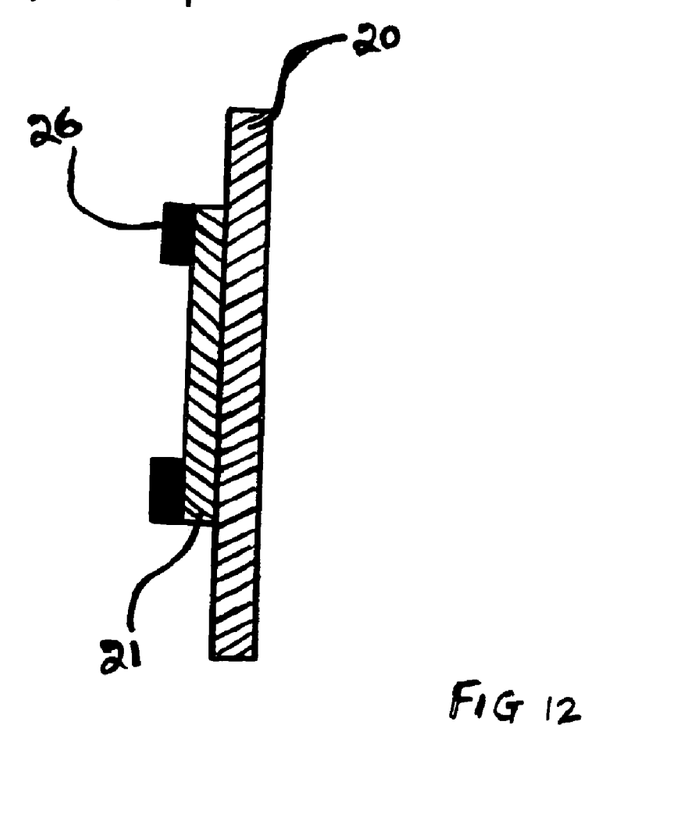
FIG. 12 Shows a cross-sectional view of the components of the first aid strip along section line 12-12 of FIG. 11.
Figure 13:
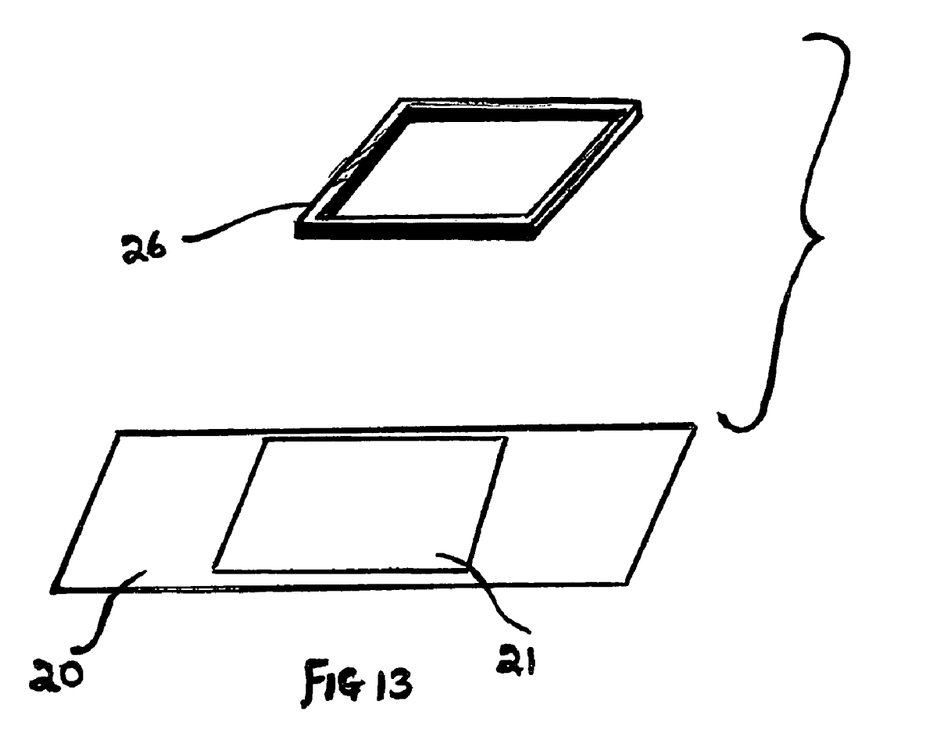
FIG. 13 Shows an exploded view of the components of the first aid strip shown in FIG. 11.

Referring now to FIG. 11 through FIG. 13, a fourth embodiment of the present invention is presented. For the presently preferred embodiment, the first aid strip comprises an adhesive tape 20, a gauze pad strip 21 attached to adhesive tape 20, and a ring 26 of inert material, like rubber, cork or latex attached to the gauze pad 21. The ring is placed over gauze pad 21 in such a way, that the outer edges of the ring 26 are flush with the edges of the gauze pad 21. For this embodiment, the ring 26 comes in contact with the skin when covering a wound.

Figure 14:
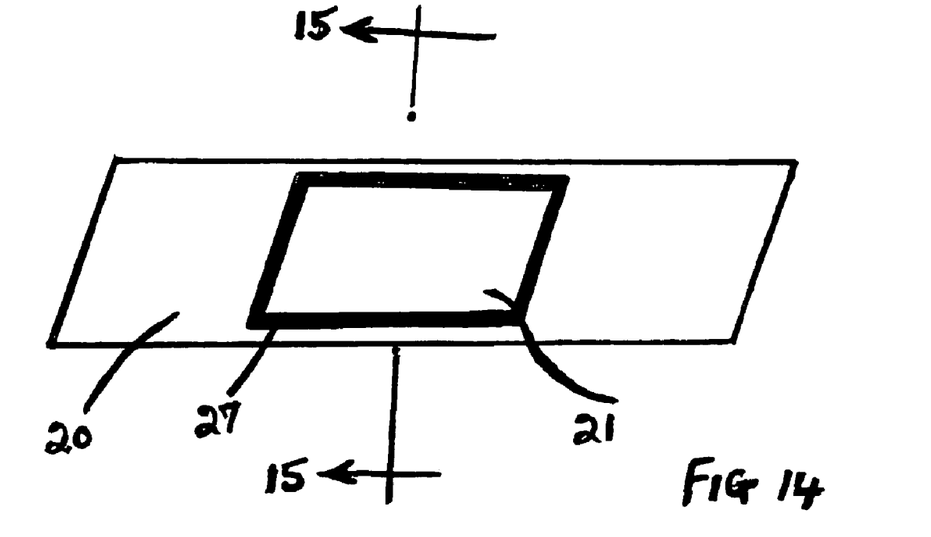
FIG. 14. Shows a tangential assembled view of a fifth embodiment of the first aid strip.
Figure 15:
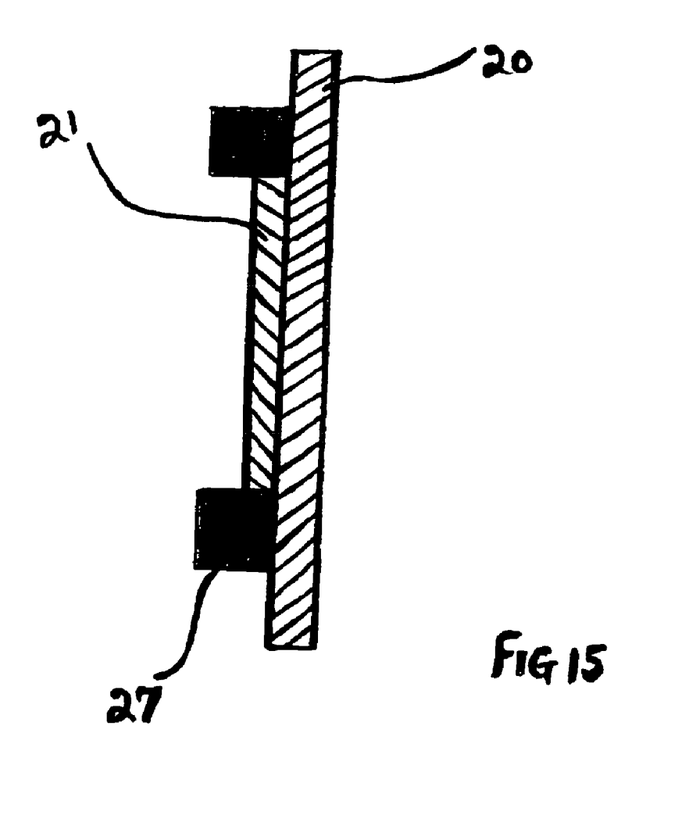
FIG. 15. Shows an cross-sectional view of the components of the first aid strip along section line 15-15 in FIG. 14.
Figure 16:
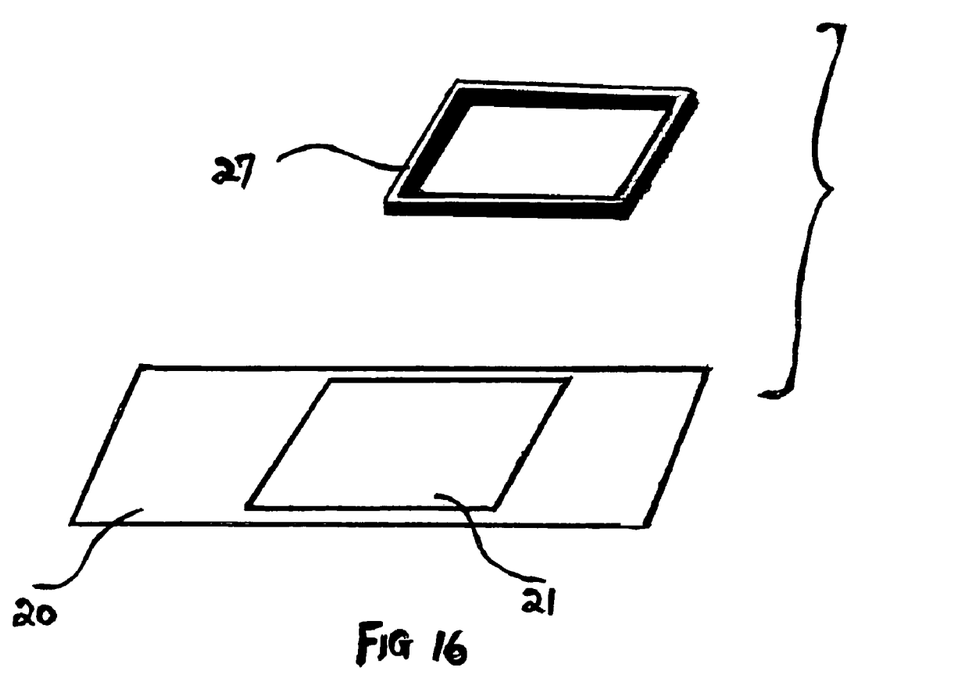
FIG. 16. Shows an exploded view of the components of the first aid strip shown in FIG. 14.

Referring now to FIG. 14 though FIG. 16, a fifth embodiment of the present invention is presented. The first aid strip in this situation has an adhesive tape 20, a gauze pad strip 21 attached to it, and a ring 27 of inert material such as cork, rubber or latex also attached to adhesive tape 20. In this embodiment the ring 27 is placed in such a way, that the inner borders of the ring surround the gauze pad strip 21. In such a situation, when the first aid strip is placed on a body, the ring 27 comes into contact with the skin. The ring surface which comes in contact with the skin may also be provided with some adhesive capability, so that it sticks to the skin. The ring 27 may have a depth of about 2.00-2.50 mm. During use, medicine can be put in the hollow created inside the ring, and the first aid strip can then be applied to the skin.

This invention extends to gauze hats/gauze caps also. It has a pouch, well, hollow or pregnant dimple or depression. It can be used with different wounds or skin conditions with an appropriate sized adhesive tape. The only difference to first aid hats/caps described above being, it does not come with its own adhesive tape. These gauze hats or gauze caps can be manufactured in the same manner as herein before described with reference to first aid strip. Although the invention has been described with reference to preferred embodiment the invention extends to all obvious modifications of the invention as claimed herein after.

Figure 17A:
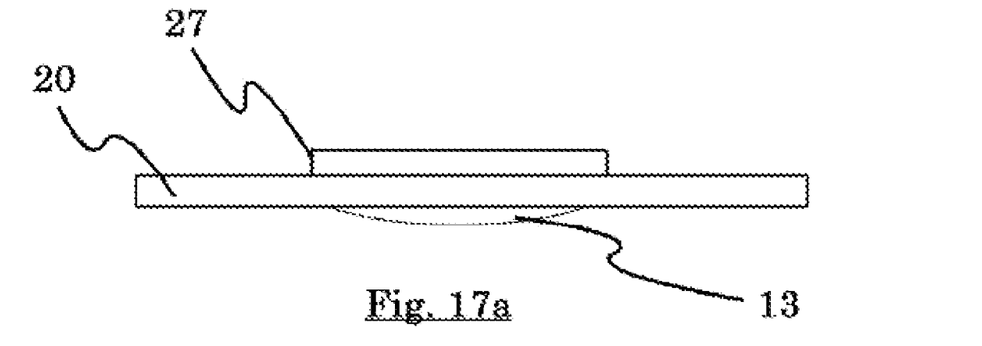
FIG. 17a Shows a side view of a sixth embodiment of the first aid strip.
Figure 17B:
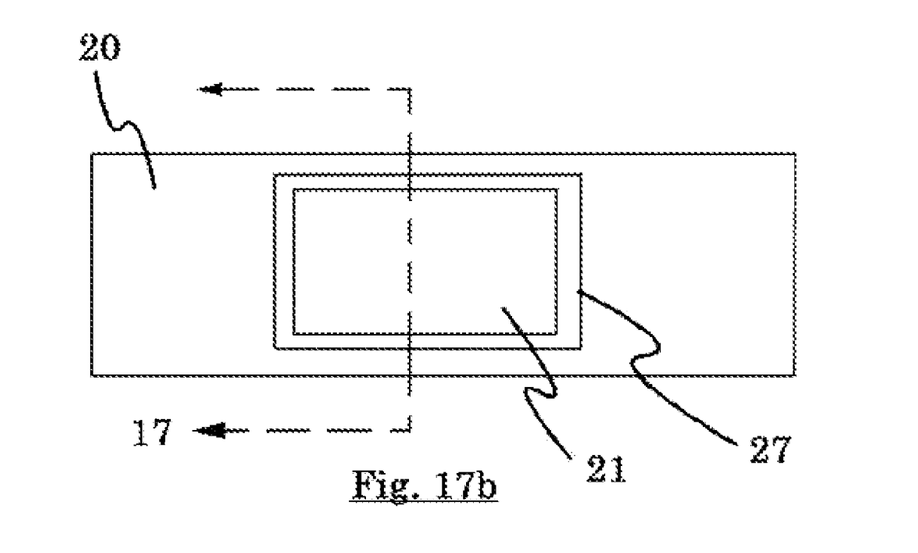
Figure 17C:
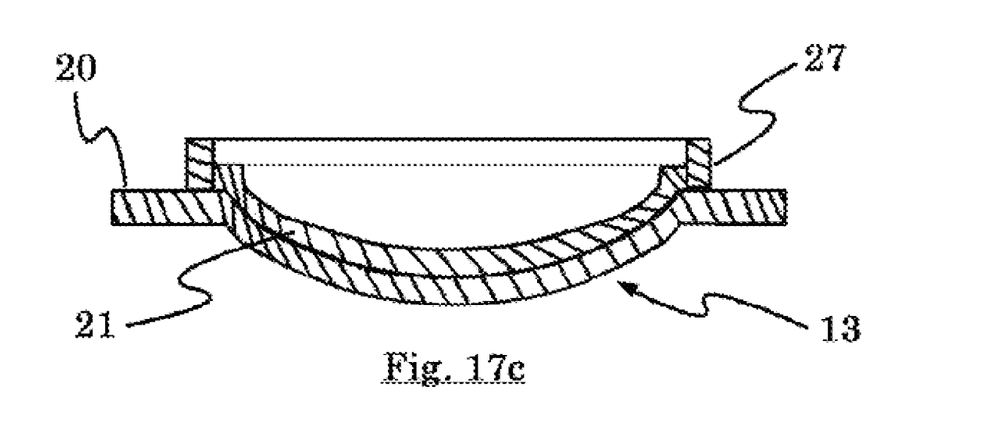
FIG. 17c Shows a cross-sectional view of the components of the first aid strip along section line 17 shown in FIG. 17b.

Referring now to FIG. 17a, FIG. 17b, and FIG. 17c, another alternative embodiment of the invention is presented by combining various aspects of the invention depicted in FIG. 9 and FIG. 10, with the inventions depicted in FIG. 14, FIG. 15 and FIG. 16. For such presently preferred embodiment of the invention, the first aid strip has an adhesive tape 20 associated with a gauze pad strip 21. Adhesive tape 20 is one embodiment of a substrate comprising a first adhesive substrate surface and an opposing second substrate surface, wherein said first adhesive substrate surface defines a substrate-geometric-figure (a rectangle for the current embodiment) and wherein said first adhesive substrate surface and said opposing second substrate surface further define a substrate-bulge extending a predefined distance away from the portions of said first adhesive substrate surface not forming said bulge.

Gauze pad strip 21 is one embodiment of a pad comprising a first pad surface and a second pad surface, wherein the distance between said first pad surface and said second pad surface define a pad-height (21h), and wherein said first pad surface defines a pad-geometric-figure that is smaller than the substrate-geometric-figure, and wherein said first pad surface and said second pad surface further define a pad-bulge extending a predefined distance away from the portions of said first pad surface not forming said pad-bulge. As depicted in the FIG. 17a-17c, the pad 21 is disposed along adhesive tape 20 so that the pad-bulge is in alignment with the substrate-bulge.

For the currently preferred embodiment, the adhesive tape 20 and gauze pad 21 both extend outwards to create a bulge (13). Restated, the first pad surface is associated with said first adhesive substrate surface so that said pad-bulge is in alignment with said substrate-bulge and so as to create a first aid strip bulge and further defining a substrate-surface-border-region around said pad.

Ring 27 is disposed on adhesive tape 20 in such a way that the inner borders of the ring surround the gauze pad strip 21. Thus, ring 27 may comprise a first ring surface and a second ring surface, wherein the distance between said first ring surface and said second ring surface define a ring depth or height (27h), and wherein said first ring surface defines a ring-geometric-figure that is smaller than the substrate-geometric-figure but larger than the pad-geometric-figure so that the first ring surface may be associated with said substrate-surface-border-region thereby surrounding said pad 21. It should be appreciated that height (27h) defined by ring (27) may be equal to or greater than height (21h) defined by pad (21).

As before, Ring 27 may be constructed from any suitable inert material including cork, rubber, and latex.

It should be noted that for such embodiment, when the first aid strip is placed on a body, the ring 27 comes into contact with the skin. The ring surface which comes in contact with the skin may also be provided with some adhesive capability, so that it sticks to the skin. The bulge (13) preferably has a depth of about 2.00-2.50 mm.

While the present subject matter has been described in detail with respect to specific embodiments thereof, it will be appreciated that those skilled in the art, upon attaining an understanding of the foregoing may readily adapt the present technology for alterations to, variations of, and equivalents to such embodiments. Accordingly, the scope of the present disclosure is by way of example rather than by way of limitation, and the subject disclosure does not preclude inclusion of such modifications, variations, and/or additions to the present subject matter as would be readily apparent to one of ordinary skill in the art.

What is claimed is as follows:

1. A bandage for covering a wound, said bandage comprising:
   a substrate comprising a first adhesive substrate surface and an opposing second substrate surface;
   a spacer comprising a first spacer surface and a second spacer surface wherein said spacer surfaces form a spacer border surrounding a spacer void in the approximate center of said spacer and wherein said first spacer surface is associated with said first adhesive substrate surface; and
   a pad comprising a first pad surface and a second pad surface wherein said first pad surface is associated with said second space surface and said first adhesive substrate surface thereby sealing said spacer between said substrate and said pad.

2. The bandage for covering a wound as in claim 1, wherein said substrate, said pad, and said spacer each define a rectangle and wherein:
(a) the length of said substrate is about three times the length of said pad,
(b) the width of said substrate is wider than the width of said pad,
(c) the length of said spacer is about the same as the length of said pad, and
(d) the width of said spacer is about the same as the width of said pad.

3. The bandage for covering a wound as in claim 1, wherein said substrate, said pad, and said spacer each define a rectangle and wherein:
(a) the length of said substrate is about three times the length of said pad;
(b) the length of said spacer is about the same length as said pad;
(c) the width of said spacer is about the same as the width of said substrate; and
wherein the width of said pad is one of (i) substantially equal to the width of said substrate, and (ii) wider than the width of said substrate.

4. The bandage for covering a wound as in claim 1, wherein said spacer is composed of inert material.

5. The bandage for covering a wound as in claim 1, wherein said spacer void defines a pouch that is about 2.0 mm to about 2.5 mm wide and about 2.0 mm to about 2.5 mm deep.

* * * * *